(12) United States Patent
Gervay-Hague et al.

(10) Patent No.: US 6,498,277 B1
(45) Date of Patent: Dec. 24, 2002

(54) DISULFONE REAGENTS AND METHODS OF PREPARING AND USING SAME

(75) Inventors: Jacqueline Gervay-Hague, Tucson, AZ (US); Michael J. Hadd, Tucson, AZ (US)

(73) Assignee: The Arizona Disease Control Research Commission, Phoenix, AZ (US)

( * ) Notice: Subject to any disclaimer, the term of this patent is extended or adjusted under 35 U.S.C. 154(b) by 0 days.

(21) Appl. No.: 09/595,048

(22) Filed: Jun. 14, 2000

Related U.S. Application Data

(60) Provisional application No. 60/138,986, filed on Jun. 14, 1999.

(51) Int. Cl.$^7$ .......................... C07F 9/02; C07C 315/00; A01N 61/00
(52) U.S. Cl. .................. 568/11; 568/28; 514/1
(58) Field of Search ................. 514/1; 568/11, 568/28

(56) References Cited

PUBLICATIONS

Einhorn L.H., et al., "Long–Term Results in Combined–Modality Treatment of Small Cell Carcinoma of the Lung.", Sem. Oncol. 5, 309–313, (1978).
Bolscher J., et al., "Decreased Fucose Incorporation in Cell Surface Carbohydrates is Associated with Inhibition of Invasion.", Clinical and Experimental Metastasis, 7(5), 557–569, (1989).
Yamada N., et al., "Increased Sialyl Lewis A Expression and Fucosyl Transferase Activity with Acquisition of a High Metastatic Capacity in a Colon Cancer Cell Line.", British J. of Cancer, 76(5), 582–587. (1997).
Izumi Y., et al., "Correlation of Cell Surface Sialyl–LeX, Fucosyltransferase Activity and Experimental Liver Metastasis of Human Colon Carcinoma Cells.", Clinical and Experimental Metastasis, 14(supplement I), 94–95, (1996).
Handa K., et al., "P–Selectiin–Dependent Adhesion of Human Cancer Cells: Requirement For Co–Expression of a 'PSGL–1–Like' Core Protein and the Glycosylation Process for Sialosyl–Lex or Sialosyl–Lea.", Int. J. Oncol, 6, 773–81, (1995).
Stone J.P. and Wagner D.D., "P–Selectin Mediates Adhesion of Platelets to Neuroblastoma and Small Cell Lung Cancer.", J. Clin. Invest., 92, 804–13, (1993).
Huang H., et al., "Structure of a Covalently Trapped Catalytic Complex of HIV–1 Reverse Transcriptase: Implications for Drug Resistance.", Science, 282, 1669–1674, (1998).
Zhao H., et al., "Arylamide Inhibitors of HIV–1 Integrase.", J. Med. Chem. 40, 1186–1194, (1997).
Lin Z., Neamati N., Zhao H., et al., "Chicoric Acid Analogues as HIV–1 Integrase Integrase Inhibitors.", J. Med. Chem., 42, 1401–1414, (1999).
Castro A. and Spencer T.A., "Formation and Alkylation of Anions of Bis(methylsulfonyl)methane.", J. Org. Chem., 57, 3496–3499, (1992).
Davidson A.H., et al., "Wittig Reactions of Unprotected Aldohexoses: Formation of Optically Active Tetrahydrofurans and Tetrahydropyrans.", Tetrahedron Lett., 29, 693–696, (1988).
Blanchette M.A., et al., "Horner–Wadsworth–Emmons Reaction: Use of lithium chloride and an amine for base–sensitive compounds" Tetrahedron Letters, 25(21), 2183–2186 (1984).

*Primary Examiner*—Jezia Riley
(74) *Attorney, Agent, or Firm*—Banner & Witcoff, Ltd.

(57) ABSTRACT

The present invention provides novel disulfone compounds and methods of preparing and using those compounds to further prepare biologically relevant gem-disulfone analogs of natural enzyme substrates. Methods of using a variety of disulfone compounds as reagents capable of forming symmetrical and non-symmetrical α, β unsaturated gem-disulfones are also provided. There is also provided a disulfone reagent which reacts with both aromatic and aliphatic aldehydes in good to moderate yield to give exclusively the trans isomer. In accordance with further aspects of the present invention, a methodology for stereospecifically preparing potential gem-disulfone enzyme inhibitors is provided. A synthetic design which allows easy substitution of functional groups so that a number of substrate analogs can be synthesized readily is also provided. In addition, there is provided a new class of compounds which are potential glycosyl transferase inhibitors having characteristics which can inhibit the incorporation of sialic acid and/or fucose into glycoconjugates present at the surface of certain cancer cells. Additionally, a class of potent disulfone-linked catechol-based enzyme inhibitors, such as HIV-1 integrase inhibitors, is provided.

4 Claims, No Drawings

DISULFONE REAGENTS AND METHODS OF PREPARING AND USING SAME

CROSS REFERENCE TO RELATED APPLICATIONS

This application claims benefit from provisional application Ser. No. 60/138,986 filed Jun. 14, 1999 now expired.

FIELD OF THE INVENTION

The present invention relates generally to sulfone phosphonate compounds and their use in organic synthesis and, more particularly, to disulfone bis-phosphonates and their preparation and use as reagents in the synthesis of biologically relevant disulfones.

BACKGROUND OF THE INVENTION

Enzymes are biological catalysts which mediate the great majority of biochemical reactions that occur in living organisms Enzymatically catalyzed reactions typically result in higher reaction rates, under milder reaction conditions, with much greater reaction specificity than other chemical reactions. The specific geometric configuration and identity of the chemical elements that create the reacting group of a reactant or substrate for a particular enzyme are important factors affecting whether that enzyme can catalyze a given reaction Typically, the amino acids which constitute the enzyme's substrate-binding site form a pocket, or cleft, in the surface of the enzyme which is geometrically and electronically complementary to the particular shape and charge distribution of the substrate's functional groups. Thus, a substrate having the wrong charge distribution, stereochemistry, chirality, et cetera will not fit into the enzymatic binding site.

The highly specific nature of enzyme-substrate binding renders enzymatic reactions particularly susceptible to influence by other substances. Compounds that can combine with an enzyme and/or its substrate may affect either substrate binding or the enzyme's turnover rate A compound which reduces enzymatic activity by either of these methods is referred to as an inhibitor. In many cases, enzyme inhibitors structurally resemble an enzyme's natural substrate in at least some respects, but the reaction catalyzed by the enzyme when it is bound to its natural substrate either cannot achieve its normal product or will do so at a considerably reduced rate, Such inhibitors are frequently referred to as analogs. Inhibitors can act through several mechanisms, two of which are competitive inhibition and noncompetitive inhibition.

A compound can be a competitive inhibitor of an enzyme if that compound competes directly with a natural substrate for an enzyme's binding site. Structurally, this type of inhibitor usually is sufficiently similar to the normal or natural substrate to enable binding to the enzyme active site, but the inhibitor differs from the natural substrate in that it is comparatively unreactive when bound to the enzyme. Since most competitive inhibitors reversibly bind their target enzyme, such compounds tend to reduce the cellular concentrations of free enzyme available for natural substrate binding, thereby inhibiting productive enzymatic activity and reducing the availability of enzyme reaction products. Inhibitors which irreversibly bind an enzyme active site are referred to as inactivators, or suicide inhibitors, and their effects on free enzyme concentration levels are much longer lived.

A substance may be deemed a noncompetitive inhibitor of an enzyme if the substance can bind the enzyme-substrate complex directly but cannot bind the free enzyme. This inhibitory mechanism likely functions by distorting the structure of the active site and rendering the enzyme incapable of catalyzing the reaction with the substrate. A noncompetitive inhibitor need not resemble the substrate at all, for it has no affect on an enzyme's ability to bind the natural substrate As such, the noncompetitive inhibitor acts by interfering with an enzyme's catalytic function, not its ability to bind its natural substrate. Since substrate binding is relatively unaffected, this type of inhibition is thought to occur more frequently in the case of multisubstrate enzymes, such as transferase enzymes which catalyze reactions that transfer a specific functional group from one substrate to another.

As enzymatic reactions often play an important role in a variety of biochemical pathways that affect biological systems, enzymes frequently are good targets for strategic efforts to affect disease processes, such as cancer, or viral invasions of a host system, such as by the human immunodeficiency virus (HIV). For example, small cell lung cancer (SCLC), a highly malignant carcinoma that is prevalent in cigarette smokers, has been found to be particularly sensitive to chemotherapy, and there are a number of combination therapies currently in clinical use. Chemotherapeutic agents currently under investigation include camptothecan derivatives, which have been found to inhibit DNA topoisomerase I, and taxol, which is an antitubular agent. While these therapies generally are thought to hold promise for inhibiting cancer cell growth and proliferation in a particular tissue or organ, they do not speak to the issue of cancer metastasis. Metastasis is the, mechanism by which cancer cells travel or spread from one area of the body to other, often unrelated, areas, thereby resulting in the development of malignant tumors throughout the body. Tumor metastasis is believed to be one or the leading causes of cancer-related mortality. Since SCLC is a form of cancer that is characterized by early onset of metastatic spread, making it a very difficult cancer to cure, the development of new chemotherapeutics which target invasion and metastasis of malignant cells is a particularly important strategy for combating this type of cancer.

Generally, cancer develops in four principle stages: (1) initiation; (2) promotion of cell growth; (3) invasion and metastasis; and (4) death of the host. Initiation is characterized by hyperproliferation of cells which then continues during the growth stage. During invasion and metastasis, tumors form and the cancer spreads to other tissues. Different forms of cancer respond differently to the variety of treatment protocols, depending upon the type and developmental stage of the cancer. In the case of SCLC, for example, the three primary methods of treatment include surgical removal of cancerous tissue, radiation therapy, and chemotherapy.

Sialyl Lewis X is a cell surface glycoconjugate that serves as a recognition element in cancer metastasis. Structurally, sialyl Lewis X is a tetrasaccharide consisting of N-acetyl neuraminic acid (NeuAc) α-(2→3) linked to galactose, which in turn is β-(1→4) linked to a glucosamine bearing an α-(1→3) linked fucose residue. Sialyl Lewis X is synthesized in the Golgi apparatus, which is located in the cytoplasm of the cell. As illustrated by the following Reaction Equation,

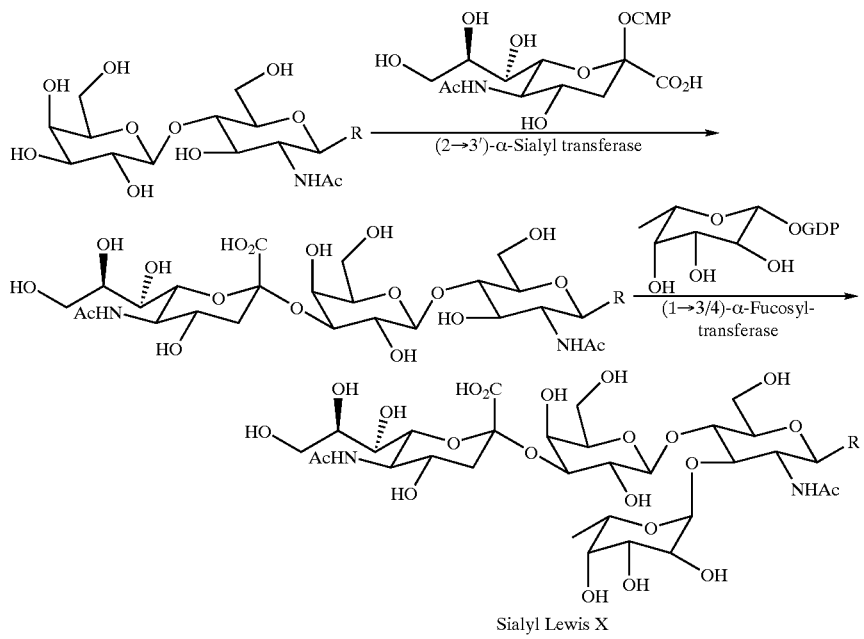

Sialyl Lewis X preparation of sialyl Lewis X begins when an activated sialyl residue (CMP-NeuAc) is transferred to lactosamine using a 2→3-sialyl transferase enzyme. Subsequently, activated fucose (GDP-fucose) is transferred to the molecule by a fucosyl transferase enzyme The resultant tetrasaccharide is then transported out of the Golgi and to the cell surface. Once at the cell surface, sialyl Lewis X serves as a cell recognition element for other molecules, such as selectin proteins (P-selectins), which are on the surface of other cells. Thus, cells having P-selectins at their surface, for example, are able to recognize and adhere to cells which have sialyl Lewis X on their surface. Studies have shown that selectin recognition of sialyl Lewis X at the cell surface is most efficient when both the fucosyl and sialyl residues are present on the sialyl Lewis X molecule. (See eg., Einhorn L. H, Bond W. H., Hornback N., and Joe B. T. "Long-Term Results in Combined-Modality Treatment of Small Cell Carcinoma of the Lung." *Sem. Oncol.* 1978, 5, 309–313; Bolscher J., Bruyneel E., Rooy H., Schallier D., Marcel M., and Smets L. "Decreased Fucose Incorporation in Cell Surface Carbohydrates is Associated with Inhibition of Invasion." *Clinical and Experimental Metastasis.* 1989, 7(5), 557–569; Yamada N., Chung Y. S., Takatsuka S., Arimoto Y., Sawada T., Dohi T., and Sowa M. "Increased Sialyl Lewis A Expression and Fucosyl Transferase Activity with Acquisition of a High Metastatic Capacity in a Colon Cancer Cell Line." *British J. of Cancer* 1997, 76(5), 582–587).

An abundance of evidence links the presence of fucosyl and sialyl residues at the surface of cancer cells to both metastatic potential and patient survival. (See e.g., Izumi, Y., Nemoto Y.; Kawamura Y., Nakatsugawa S., Dohi T., Oshima M., Irimura T. "Correlation of Cell Surface Sialyl-LeX, Fucosyltransferase Activity and Experimental Liver Metastasis of Human Colon Carcinoma Cells" Sixth International Congress of the Metastasis Research Society, Gent, Belgium, Sep. 8–11, 1996. *Clinical and Experimental Metastasis* 1996, 14(supplement I), 94–95.) This evidence serves to highlight the significance of sialyl- and fucosyl-transferases, the enzymes which mediate the transfer of these residues to cell surface glycoconjugates, as key targets for chemotherapeutic intervention.

Generally, tumor metastasis is facilitated by cell-cell adhesion and communication, which is accomplished through interactions between molecules expressed on the cells' surface, For example, studies have shown that, during metastasis, many carcinoma cells interact with certain proteins, such as the P-selectins, found on the surface of blood platelets (thrombocytes). (See e.g., Handa K., White T., Ito K., Fang H., Wang S-S., Hakomori S-I. "P-Selectin-Dependent Adhesion of Human Cancer Cells: Requirement For Co-Expression of a 'PSGL-1-Like' Core Protein and the Glycosylation Process for Sialosyl-Lex or Sialosyl-Lea" *Int. J. Oncol.* 1995, 6, 773–81 and references cited therein; Stone J. P., and Wagner D. D. "P-Selectin Mediates Adhesion of Platelets to Neuroblastoma and Small Cell Lung Cancer" *J. Clin. Invest.* 1993, 92, 804—13). This evidence suggests that the ability of malignant cells to bind particular proteins, such as the selectins, mediates the transport of those cells through the body. Thus, if selectin binding by cancer cells can be inhibited or prevented, it is likely that metastasis of malignant cells can be slowed or eliminated. Since the presence of fucose and/or sialic acid on sialyl Lewis X has been shown to facilitate selectin recognition at the cell surface, and since selectin binding has been demonstrated to mediate metastasis, it is highly likely that fucose and/or sialic acid are important recognition elements in tumor metastasis. Thus, if either fucose or sialic acid is prevented from being incorporated into cancer cell surface glycoconjugates, P-selectin binding can be inhibited, and tumor metastasis can be slowed or prevented entirely. Cumulatively, this research indicates that the development of enzyme substrate analogs designed to target and effectively inhibit the transferase enzymes that facilitate the incorporation of either fucose or sialic acid into cancer cell-surface glycoconjugates is a viable strategy for impeding or eliminating these important metastatic pathways.

Enzyme inhibitors also can be used to affect undesirable biochemical processes in the context of human immunodeficiency virus (HIV) infection. The lifecycle of HIV has seven distinct phases: (1) viral binding to host cell receptors; (2) entry of the viral core into host cells; (3) shedding of the viral core; (4) reverse transcription of viral RNA into viral DNA; (5) integration of viral DNA into host DNA; (6) viral DNA replication and protein synthesis; and (7) budding of new viral cores. Current drug therapies for the treatment of HIV focus on two of these phases by inhibiting to key enzymes, HIV-reverse transcriptase (HIV-RT) and HIV-protease.

HIV-RT is an enzyme endogenous to retroviruses that has two known catalytic duties. It functions as an RNA or DNA dependent DNA polymerase and as a ribonuclease H. Currently, only the polymerase activity has been targeted for enzyme inhibition. HIV-RT inhibitors block the transcription of viral RNA into viral DNA These inhibitors were the first HIV inhibitors approved by the FDA, but viral resistance to their activity tends to develop over time, thereby limiting their use as a sole therapy. The first drug approved for treatment of HIV infection was AZT (3'-azido-3'deoxythymidine), a compound in which the natural 3'-OH of thymidine is substituted with an azide. This azide functionality eliminates the possibility of covalent elongation of a growing DNA strand by functioning as a chain terminating inhibitor. Since the active form of AZT includes a 5'-triphosphate, which is synthesized and added in vivo by endogenous host enzymes after the uncharged form of the compound has been transported across the cell membrane, AZT is properly characterized as a prodrug.

One of the major drawbacks of currently available chain terminating nucleoside inhibitors is the high mutation rate of HIV-RT, which promotes viral resistance to the available inhibitor therapies. A recent study by Harrison and Verdine (Huang H., Chopra R., Verdine G., Harrison S. C. "Structure of a Covalently Trapped Catalytic complex of HIV-1 Reverse Transcriptase: Implications for Drug Resistance" *Science* 1998, 282, 1669–1674) demonstrated that the binding pocket of the catalytic complex of HIV-RT is a 3'-binding pocket and that this pocket incorporates point mutations in those enzymes that are resistant to AZT as well as other nucleoside analog inhibitors. Although extensive research has focused on the use of various 3'-analogs of nucleosides, much less attention has focused on altering the 5'-triphosphate moiety of the natural nucleoside triphosphate substrates.

Another class of approved compounds is HIV-protease inhibitors, which interfere with the processing of viral proteins. Combination therapy of protease inhibitors and RT-inhibitors has proven promising in some cases; however, the search for less toxic and more potent candidates in both of these classes continues. As combination therapy is the most promising approach to HIV treatment to date, identification of other key enzymes that can be targeted for chemotherapeutic intervention is needed.

One of the most recently targeted enzymes for anti-HIV therapy has been the HIV integrase HIV-IN) enzyme. This enzyme integrates newly formed viral DNA into host DNA by inserting the viral DNA product of the reverse transciptase and viral RNA reaction into the host's chromosomes. As no cellular counterpart to this enzyme has been identified, it is an attractive target for chemotherapeutic intervention because compounds directed at its inhibition are unlikely to interfere with or affect the functioning of the host system. Catechol-based analogs, which may be exemplified by the following Formula,

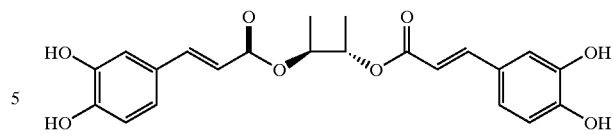

comprise one class of compounds that have been identified as having potent anti-HIV-IN activity. Recent studies based on a large number of these HIV-IN inhibitors have shown that catechol-based inhibitors have several general structural features in common: (1) the presence of two aryl units, (2) separated by a central linker, (3) with at least one aryl ring having an ortho bis-hydroxylation pattern (Zhao i., Neamati N., Mazumder A., Sunder S., Pommier Y., ad Burke T. "Arylamide Inhibitors of HIV-1 Integrase" *J. Med. Chem.* 1997, 40, 1186–1194) The inhibitory potency of compounds in this general class has been demonstrated repeatedly, and development of improved catechol-based HIV-IN inhibitors holds promise for chemotherapeutic intervention in the progression of HIV infection (Zhao H., Neamati N., Mazumder A., Sunder S., Pommier Y., ad Burke T. "Arylamide inhibitors of HIV-1 Integrase" *J. Med. Chem.* 1997, 40, 1186–1194; Lin Z., Neamati N., Zhao H., et al. "Chicoric Acid Analogues as HIV-1 Integrase Inhibitors" *J. Med. Chem.* 1999, 42, 1401–1414). Thus, in the field of HIV research as well as cancer research, the successful development of enzyme substrate analogs to inhibit particular target enzymes is a viable strategy for either elating or slowing the progression of the disease.

A well-designed substrate analog or competitive inhibitor should be capable of passing through the cell membrane, being recognized by the target enzyme, binding the enzyme successfully, not reacting in a manner that will yield the undesirable biochemical product, and riot degrading or hydrolyzing within the environment of the cell. For example, in the case of targeting SCLC tumor metastasis when developing successful competitive inhibitors of sialyl transferase or fucosyl transferase, the inhibitor or analog should structurally resemble the relevant nucleotide sugar substrate in many respects. A nucleotide sugar is the glycosyl or sugar donor in biosynthetic reactions catalyzed by glycosyl transferases. Nucleotide sugar substrates consist of the relevant carbohydrate residue (sialic acid for sialyl transferase and fucose for fucosyl transferase) linked to the relevant activating nucleoside mono- or diphosphate (cytidine and guanosine, respectively). In most cases, the link between the carbohydrate residue and the nucleoside phosphate is either a mono- or a diphosphate linkage, which, in either case, results in the sugar being linked to the other components via at least one phosphodiester bond. Additionally, the 5-bond distance between the sugar and the 5'-nucleoside residue must be maintained, since this distance has been shown to be critical for achieving enzyme-substrate binding. These basic components, that is, the carbohydrate residue, the nucleoside phosphate, and the linking group need to be present in the inhibitor, otherwise the inhibitor cannot be recognized and bound by the target enzyme. However, because the phosphodiester bond connecting the sugar to the nucleoside is a highly labile bond, replacing the oxygen atom linkage in that bond with a carbon atom linkage, creating what is known as a C-glycoside, rather than the natural O-glycoside, often tends to create a more robust analog under physiological conditions. However, incorporation of the carbon atom presents its own set of constraints. In order for a C-glycoside to fit into the enzyme active site, the carbon atom must be incorporated in an equatorial rather than an axial position so that the molecule maintains the appropriate stereochemistry needed for complexation with the enzyme. The challenge, therefore, lies in designing and implementing chemical substitutions within the natural substrate molecule to impart all the above-noted characteristics to an inhibitor.

There are several prior art examples of glycosyl transferase inhibitors, including tunicamycin, a naturally occurring antibiotic which is an isosteric analog of nucleoside diphosphates. However, because tunicamycin is highly toxic, researchers have sought alternative isosteres of this compound. One design strategy has been to produce analogs with a more stable functionality than the extremely labile diphosphate linkage, while still retaining the critical 5-bond distance between the sugar and the 5'-nucleoside residue. To date, both O-linked and C-linked glycosidic analogs of the nucleoside diphosphates have been developed. However, while the prior art glycosyl transferase analogs have been shown to actively inhibit the target enzyme, they have proved to be unsatisfactory in vivo in several regards. First, as with tunicamycin, toxicity may present a problem. Second, the oxygen atom linkages comprised by the molecules frequently result in enzymatic cleavage of the molecule within the cellular environment. Finally, the presence of a formal charge on the molecule often precludes its successful transport across the cell membrane.

In the light of the known disadvantages of prior art substrate analogs, phosphate linkages present in many enzyme substrates have been recognized as likely sites for altering the chemistry of the natural substrate in a manner which would result in a successful inhibitor compound. Depending on the targeted enzyme substrate, these phosphate linkages may be mono-, di-, or triphosphate linkages. Among the reasons for identifying the phosphate linkage as a site for chemical substitution is that the phosphate moiety itself is unsuitable in a substrate analog inhibitor because it is easily hydrolyzed or cleaved by other enzymes present within the cell and, as an ionic or charged moiety, it generally has difficulty in crossing cell membranes, which are lipophilic.

Sulfones have been recognized in the literature as substitutes for phosphate moieties, such as biological phosphodiesters, in a variety of contexts. (Castro A. and Spencer T. A. "Formation and Alkylation of Anions of Bis(methylsulfonyl)methane." *J. Org. Chem.* 1992, 57, 3996–3499) In particular, the disulfone moiety has been recognized as a good potential surrogate for the diphosphate group present in a variety of natural enzyme substrates for several reasons: (1) the disulfone moiety is not readily hydrolyzed; (2) disulfones presumably have less difficulty in crossing the cell membrane due to their electrical neutrality; (3) disulfones are generally similar in size and shape to the corresponding diphosphates; and (4) disulfones likely are sufficiently polar to bind the enzyme active site in the place of an ionic diphosphate moiety. (Id) Despite recognition of the usefulness of disulfones, prior art disulfone reagents and methods of preparing substrate analogs for certain enzymes have been generally unsatisfactory, as the design and preparation of a suitable disulfone reagent capable of being used to synthesize stereospecific substrate analogs in an acceptable yield has proved elusive. For example, the use of gem-disulfones as pyrophosphate analogs was initially investigated by Spencer in his attempt to produce farnesyl transferase inhibitors (Castro A. and Spencer T. A. "Formation and Alkylation of Anions of Bis(methylsulfonyl) methane." *J. Org. Chem.* 1992, 57, 3996–3499). However, the highly basic di- and tri-anion chemistry employed in Spencer's syntheses resulted in low yields and produced compounds with no resultant biological activity. Thus, an important reason for the reported unacceptable yields of disulfone analogs is that known reagents and reaction sequences require strongly basic conditions which ultimately degrade the target molecule over the course of the reaction.

However, the disulfone moiety is extremely versatile, and its application in the synthesis of relevant enzyme inhibitors goes beyond its ability to substitute for the phosphate moiety frequently present in natural substrates. For example, in the case of HIV-1 inhibition, the disulfone moiety can be used to synthesize effective HIV-integrase inhibitors by serving as the central linker between the two aryl units of a catechol derivative. Many catechol-based inhibitors have been shown to inhibit HIV-IN effectively in cell-free assays. However, many of these inhibitors exhibit collateral cellular toxicity, which is thought to be caused by either their oxidation to reactive quinone species or, perhaps, catabolism to cytotoxic metabolites. Other catechol inhibitors may be characterized as prodrugs, since they would rely on host enzymes to convert them to their active inhibitory form after they have been transported across the cell membrane in an electrically neutral, inactive form. Still other catechol derivatives would exhibit a short half-life, metabolizing very quickly and affecting free enzyme concentrations for only limited periods of time.

In view of the foregoing, a need exists for suitable reagents and methods of preparing biologically relevant enzyme inhibitors which overcome the shortcomings of the prior art.

SUMMARY OF THE INVENTION

In accordance with the principles of the present invention, a disulfone compound is provided, Methods of preparing various disulfone compounds are also provided. Methods of using a variety of disulfone compounds as reagents capable of forming symmetrical and non-symmetrical α, β unsaturated gem-disulfones are also provided. There is also provided a disulfone reagent which reacts with both aromatic and aliphatic aldehydes in good to moderate yield to give exclusively the trans isomer.

In accordance with further aspects of the present invention, a methodology for stereospecifically preparing potential gem-disulfone enzyme inhibitors is provided. A synthetic design which allows easy substitution of functional groups so that a number of substrate analogs can be synthesized readily is also provided. In this regard, a reagent which is capable of incorporating a disulfone moiety into a sugar nucleoside so that a suitable substrate analog can be synthesized is also provided. Inhibitors of diphosphate-dependent enzymes, such as enzymes which catalyze the metastatic pathways of certain cancers like small cell lung cancer are also provided. In addition, there is provided a new class of compounds which are potential glycosyl transferase inhibitors. Potential chemotherapeutics which will inhibit the incorporation of sialic acid and/or fucose into glycoconjugates present at the surface of certain cancer cells are also provided. Additionally, a class of potent catechol-based enzyme inhibitors, such as HIV-1 integrase inhibitors, is provided.

Other objects, features, and advantages of the present invention will become apparent to those skilled in the art from the following detailed description. It should be understood, however, that the detailed description and specific examples, while indicating exemplary embodiments of the present invention, are given for purposes of illustration only and not of limitation. Many changes and modifications within the scope of the instant invention may be made without departing from the spirit thereof, and the invention includes all such modifications.

DETAILED DESCRIPTION OF EXEMPLARY EMBODIMENTS

In accordance with one embodiment, the present invention provides novel disulfone compounds and methods of preparing and using those compounds to further prepare biologically relevant gem-disulfone analogs of natural enzyme substrates. In accordance with one aspect of this embodiment of the present invention, a disulfone Compound 10 is provided that may be represented by the follows Formula:

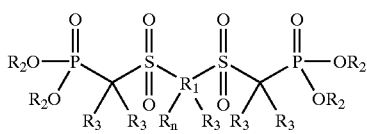

(10)

In Compound 10, n is preferably 0, 2, or 3. Preferably, $R_1$ represents a carbon atom or a nitrogen atom. Preferably, $R_2$ may be the same or different and represents any suitable chemical element or chemical group, such as hydrogen; an alkyl group of from about 1 to 4 carbons (for example, methyl, ethyl, isopropyl, and tert-butyl); or an arylalkyl group, such as a benzyl group, which can be a substituted arylalkyl group, such as a mono-, di-, tn-, tetra-, or penta-substituted benzyl group. Preferably, $R_3$ may be the same or different and represents any suitable chemical element or chemical group, such as hydrogen, a double bonded oxygen atom, a fluorine atom, a hydroxyl group, or an epoxide ring. No particular double bond geometry (for example, cis or trans) is intended by the structure of Compound 10 nor by any of the other compounds referenced below, unless specifically stated herein.

As illustrated by the following Reaction Equation A,

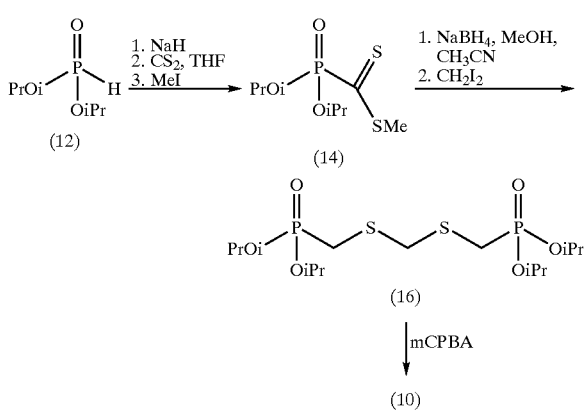

(A)

an exemplary embodiment of the novel disulfone compound in accordance with this aspect of the instant invention can be synthesized from commercially available diisopropylphosphite 12. The sodium ion of diisopropylphosphite 12 can be condensed with carbon disulfide and followed by methylation to give the dithioester 14. Selective reduction of the dithioester 14 gives the sodium thiolate which is reacted in situ with diiodomethane to give the bis-sulfide 16. Oxidation of the bis-sulfide 16 with meta-chloroperbenzoic acid (mCPBA) affords the bis-sulfone bis-pbosphonate of Compound 10. Alternatively, as illustrated by the following Reaction Equation B,

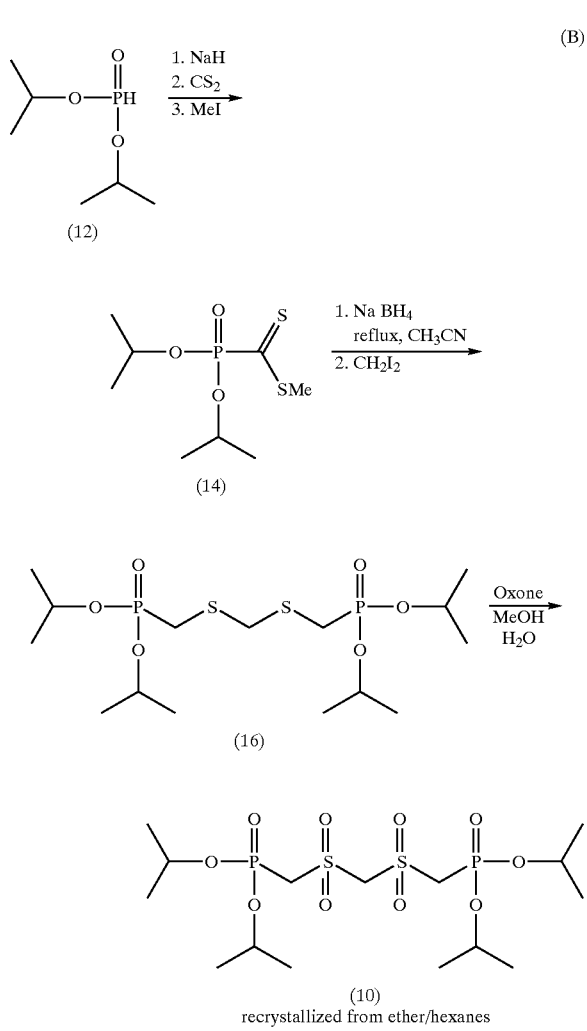

oxidation of the bis-sulfide 16 with OXONE (namely, a compound whose active ingredient is potassium peroxymonosulfate, available from DuPont under the OXONE trademark) also affords the bis-sulfone bis-phosphonate of Compound 10. Various other methods, as now known or hereafter devised, also may be utilized to produce the bis-sulfone bis-phosphonate of Compound 10.

It should be understood that the disulfone compounds of the subject invention may be modified, and, as a result, a variety of derivatives are possible and also come within the scope of the present invention. For example, derivatives of the inventive bis-sulfone bis-phosphonate compound may include a bis-sulfone carbonyl analog, represented by the formula of Compound 10, where n is 0, $R_1$ is a carbon atom, and $R_3$ is a double bonded oxygen atom and a fluorinated bis-sulfone analog, represented by the formula of Compound 10, where n is 3, $R_1$ is a carbon atom, and $R_3$ is preferably hydrogen or fluorine.

As illustrated by Reaction Equation C below, a bis-sulfone carbonyl analog can be prepared by selective reduction of 18 followed by reaction with carbonyl diimidazole to give 20 and oxidation to form the carbonylated derivative of Compound 10.

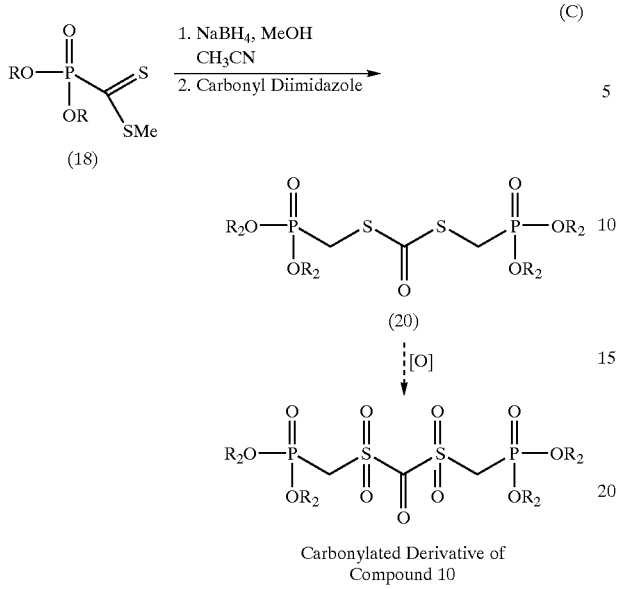

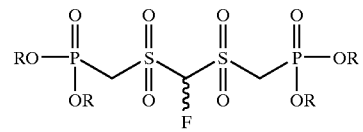

mono-Fluorinated derivative
of Compound 10

These and other derivatives of Compound 10 may be synthesized, as may be necessary, in accordance with conventional techniques.

In accordance with one embodiment of the present invention, Compound 10 may be used to synthesize biologically relevant gem-disulfones, such as analogs of target enzyme substrates for example. While the disulfone compounds of the instant invention may be modified in any number of ways for a variety of uses, the present inventors have found that the inventive compounds are particularly useful as reagents in the Horner-Emmons-Wittig reaction. In accordance with this embodiment, the bis-sulfone moiety of Compound 10 is capable of undergoing selective condensation with any suitable aldehyde, thereby producing a highly efficient route for synthesizing particular molecules of interest. For example, reacting Compound 10 with a suitably protected reducing sugar and subsequent condensation with a 5'-guanosyl aldehyde derivative gives the target differentially functionalized gem-disulfone. Alternatively, as illustrated in Table 1 below, condensation of Compound 10 with a variety of simple aromatic aldehydes and carbohydrate-based aldehydes occurs readily, and either mono- or bis-addition can be achieved, depending upon the quantity of aldehyde employed, to produce both mono- and bis-substituted α,β unsaturated gem-disulfones.

As illustrated by Reaction Equation D below, a fluorinated derivative of Compound 10 can be prepared by reacting the inventive bis-sulfone bis-phosphonate Compound 10 with hexamethyldisilazane (HMDS) and N-fluoro-O-benzendisulfonimide to form a mono-fluorinated derivative of Compound 10.

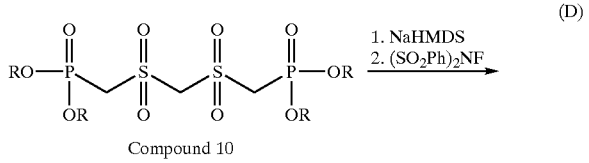

TABLE 1

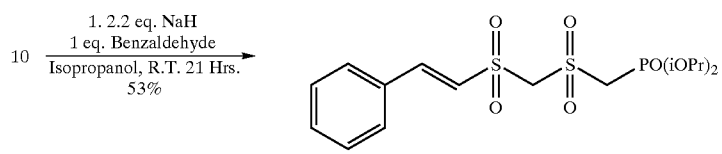

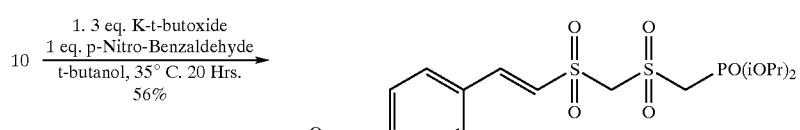

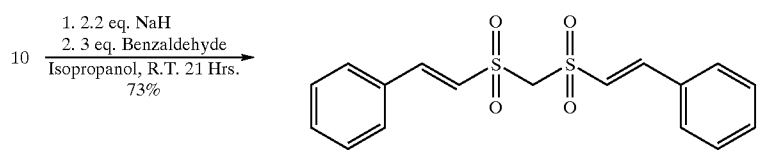

TABLE 1-continued

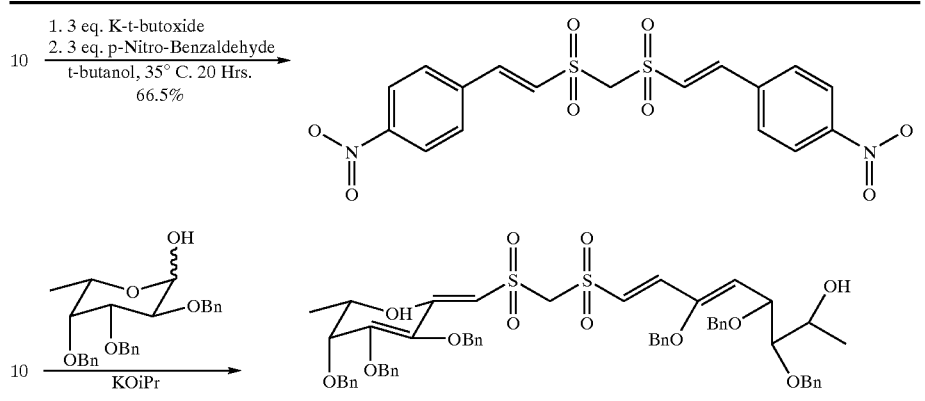

The novel disulfones of the various embodiments of the present invention can be used in a variety of ways and for a variety of purposes now known or hereafter devised by those skilled in the art. However, in accordance with one embodiment of the present invention, the novel disulfones have been found to be useful as Horner-Emmons-Wittig (HEW) reagents. In this regard, the term HEW reagent refers to the use of the novel disulfones as reagents in the Horner-Emmons-Wittig reaction (also known as the Horner-Emmons reaction) with all types of aldehyde compounds. As used herein, the term Horner-Emmons-Wittig reaction generally refers to types of condensation reactions used in organic synthesis to generate carbon-carbon bonds, producing olefins as products. In accordance with this embodiment, use of the novel disulfones as HEW reagents produces high reaction rates, good to moderate yields, and high stereoselectivities (e.g., no Z isomers were formed). As illustrated in Table 2 below (see next page), both activated and deactivated aromatic aldehydes are well-tolerated, Aliphatic substrates also undergo the condensation reaction, rendering this an efficient method for the incorporation of gem-disulfones into a variety of molecules. In this regard, the reaction conditions may be varied in any conventional manner now known or hereafter devised by those skilled in the art. For example, other bases and/or solvents as are now known or hereafter devised may be utilized. Preferred bases include, but are not limited to, the following: NaH, t-BuOLi, DIEA-LiBr, and/or suitable mixtures thereof. Preferred solvents include, but are not limited to, the following: i-PrOH, t-BuOH, THF, and/or suitable mixtures thereof.

While the novel disulfones of the present invention can be used in accordance with the various embodiments described herein to produce numerous types of compounds, the present inventors have found that use of the novel disulfones as HEW reagents yields compounds which are or may be useful due to, inter alia, their enzyme inhibition characteristics. In accordance with the instant invention design considerations for the synthesis of effective enzyme inhibitors include, but are not limited to, the following: First, inhibitors of cellular enzymes should be able to cross the cell membrane and be readily absorbed by cells; secondly, they should be stable to degradation by host enzymes so that cellular inhibitor concentrations can be maintained for a suitable period of time; and, finally, once the inhibitors bind the target enzymes, the inhibitors should effectively compete with the natural substrate without reacting and subsequently being converted to product. These criteria are illustrative only and not intended to be restrictive, as those skilled in the art will appreciate in view of the variety of modifications of these criteria that are possible, all of which are intended to be within the scope of the present invention, as hereinafter more fully described.

TABLE 2

| R | # | Base/Solvent | Time (hr) | Aldehyde:1 | Yield[d] |
|---|---|---|---|---|---|
| (phenyl) | 10 | NaH/i-PrOH | 21 | 3:1 | 73 |
| (4-nitrophenyl) | 11 | t-BuOLi/t-BuOH | 2 | 3:1 | 66 |
| (4-methoxyphenyl) | 12 | t-BuOLi/THF | 20 | 3:1 | 45 |
| (2-naphthyl) | 13 | DIEA-LiBr/THF | 20 | 1:2 | 42[a] |
| (3,4-diacetoxyphenyl) | 14 | t-BuOLi/THF | 0.5 | 3:1 | 74[b] |
| (sugar-OM) | 15 | t-BuOLi/THF | 2 | 1:1.1 | 59[c] |

In the light of these criteria, the present inventors have found that the various HEW reactions which can be carried out in accordance with the embodiments of the present invention are particularly well-suited to the synthesis of enzyme inhibitors, Those reactions which are capable of synthesizing either C-glycoside disulfone analogs of glycosyl transferase substrates or disulfone-linked catechol-based inhibitors of HIV-1 integrase are especially preferred.

In accordance with the present invention, these reactions generally proceed by reacting a novel disulfone HEW reagent with a selected aldehyde under mildly basic conditions to obtain a desired end product. In certain applications, suitable protection strategies preferably are employed to render certain functional groups on the selected aldehyde and/or other reactants unreactive. In this manner, normally reactive functional groups are less likely to undergo undesirable reactions as the condensation reaction proceeds. In such cases, generally, once the reaction produces the desired intermediate, suitable deprotection strategies are employed, as may be required, to achieve the desired end product. The specific protection and deprotection strategies employed during a given synthetic reaction sequence will depend upon, inter alia, the particular reactants used, and such strategies can be effected by any means known and practiced by those of ordinary skill in the art. Likewise, the preferred mildly basic reaction conditions can be created by any means known and practiced by those skilled in the art; however, in accordance with various aspects of the present invention, such conditions are preferably created by utilizing a source of lithium cations, such as lithium chloride or lithium bromide for example, and a suitable amine base, such as diisopropylethyl amine (DIEA), or 1,8-diazabicyclo[5.4.0]undec-7-ene (DBU). Alternatively, any suitable base having a pKa of about 15 or higher can be used. (See e.g., "Horner-Wadsworth-Emmons Reaction: Use of lithium chloride and an amine for base-sensitive compounds" *Tetrahedron Letters*, 1984, 25(21), 2183–2186). As will be appreciated by one skilled in the art, various changes and modifications to the above-described method for using novel disulfone reagents can be implemented, and the method thus modified will still come within the scope and spirit of the present invention.

Synthesis of C-Glycoside Sulfone Analogs of Enzyme Substrates

In the case of synthesizing C-glycoside disulfone analogs of glycosyl transferase substrates in accordance with preferred aspects of this embodiment of the present invention, the novel disulfone reagent and a suitably selected and, in many cases, suitably protected sugar-based aldehyde are caused to undergo condensation preferably under mildly basic conditions to produce an intermediate compound. Then, this intermediate compound and a suitably selected and, in most cases, suitably protected 5'-furanosyl aldehyde sugar also are caused to undergo condensation, preferably under mildly basic conditions, and preferably followed by global deprotection, if applicable, to yield the targeted enzyme substrate analog. In its general design the synthetic strategy thus employed conserves the five bond distance between the carbohydrate and the nucleoside. The present inventors believe this to be an important factor in maintaining the spatial requirements of the glycosyl transferase enzyme's active site. Further, as discussed in greater detail above, the O-glycoside linkage between the carbohydrate and the nucleoside preferably is substituted with a C-glycoside linkage to prevent potential cellular degradation, and the phosphate linkages are substituted with the non-labile sulfone functionalities.

Using the novel disulfone reagent of the present invention, compounds for inhibiting the incorporation of a carbohydrate residue, such as an α-L-fucose for example, into cell surface glycoconjugates have been designed and synthesized. Since sugar-based aldehydes are in equilibrium with their corresponding closed pyranose forms, excess base typically is required to achieve efficient conversion. However, since the use of excess base frequently leads to undesirable elimination, in accordance with various aspects of the present invention, deprotonation of the disulfone HEW reagent under mild conditions in the presence of lithium cations is preferably employed in the condensation reaction. For example, as illustrated by the Reaction Equation E below, utilization of either lithium chloride or lithium bromide and an amine base has been found to create tie preferred mildly basic conditions and prevent undesirable elimination resulting from possible internal deprotonation by the alkoxide formed at C-5. If an unprotected sugar 22 is employed, the allylic proton in 24 should be relatively less acidic, since the allylic hydroxyl also may be deprotonated. It should be noted, however, that in cases where the fully deprotected sugar 22 is utilized, care should be taken to ensure the formation of the desired pyranose using upon conjugate addition rather than the furanose

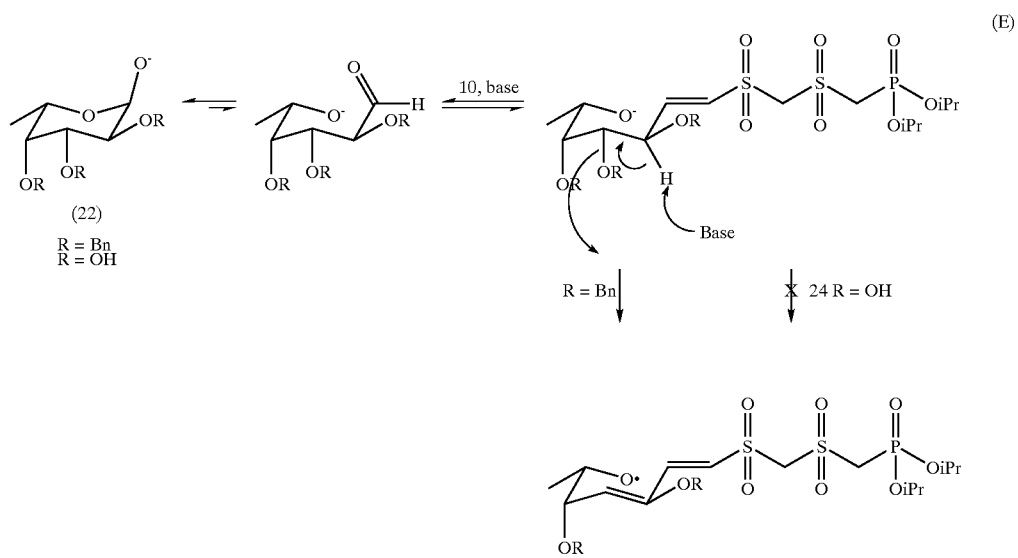

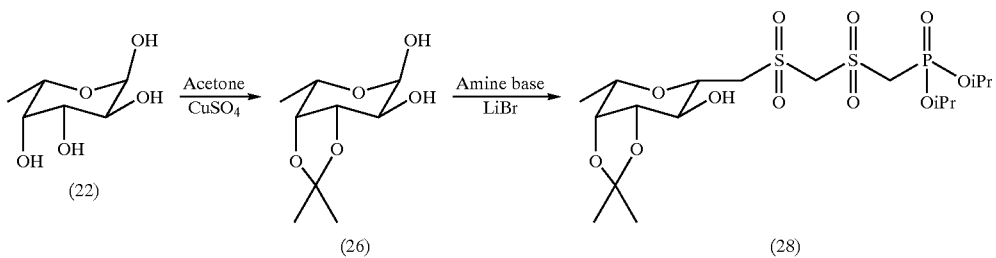

Solution 1: Use amine base, LiBr
Solution 2: Use partially protected sugar, i.e. 2-OH ring. Preferably, the disulfone reagent is reacted with 3,4-isopropylidene-D-fucose 26 under mildly basic conditions to afford 28, an exemplary protected fucosyl-C-glycoside bis-sulfone phosphonate, which can then undergo condensation with a suitably protected nucleotide sugar, such as 5'-guanosyl aldehyde for example. Under the reversible conditions of the reaction, the β-C-glycoside will form, as demonstrated by Davidson and co-workers. (See, Davidson A. H., Hughes L. R, Qureshi S. S., and Wright B. "Wittig Reactions of Unprotected Aldohexoses: Formation of Optically Active Tetrahydrofurans and Tetrahydropyrans" *Tetrahedron Lett.* 1988, 29, 693–696).

As illustrated by the following Reaction Equation F, (F)

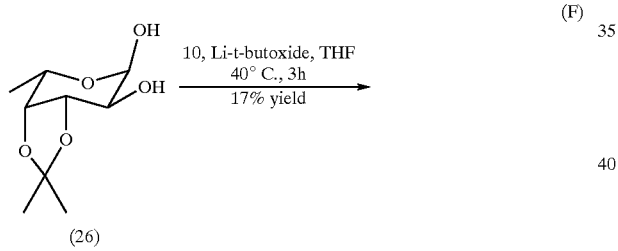

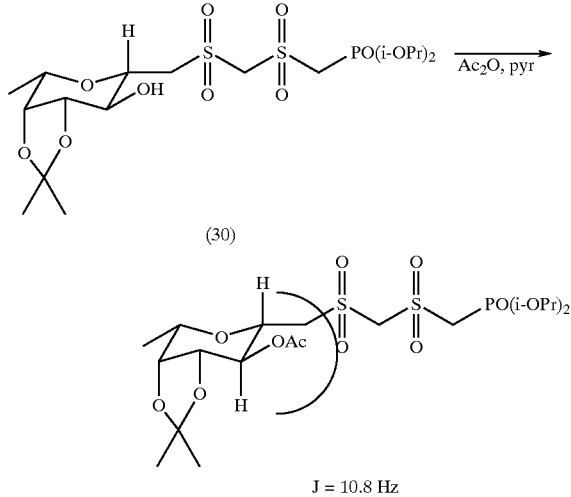

$J = 10.8$ Hz the feasibility of this transformation has been demonstrated, and 30 has been produced in an unoptimized 17% yield.

As illustrated by the following Reaction Equation G, (G)

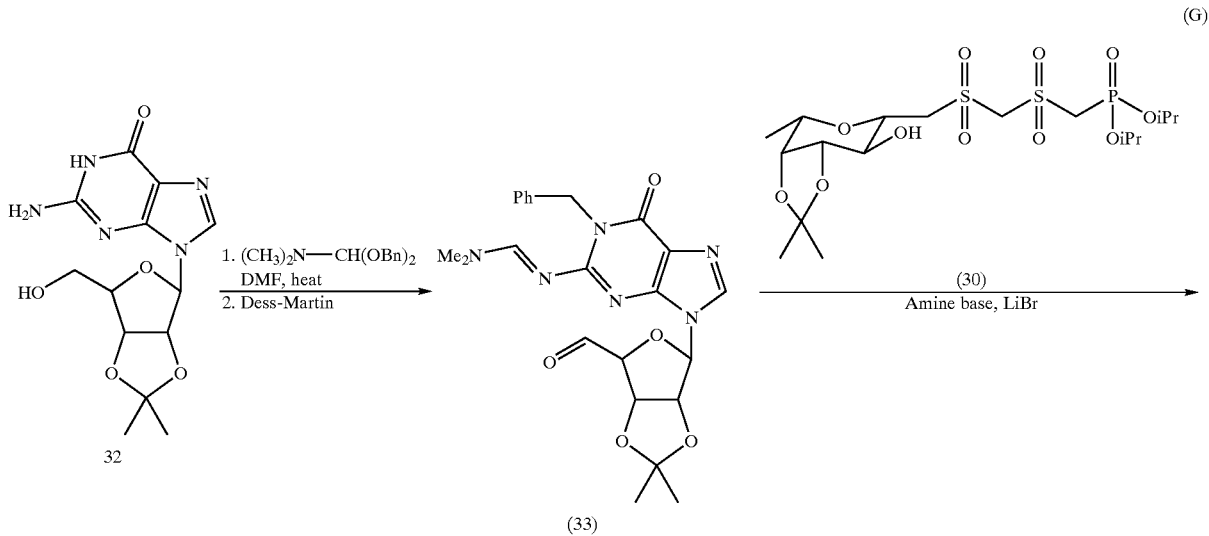

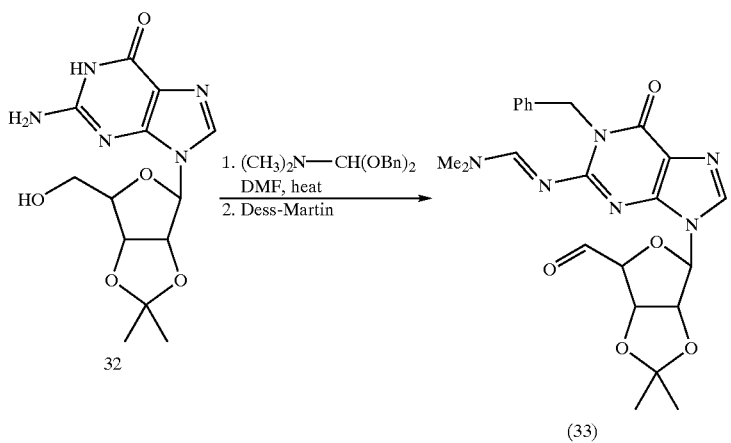

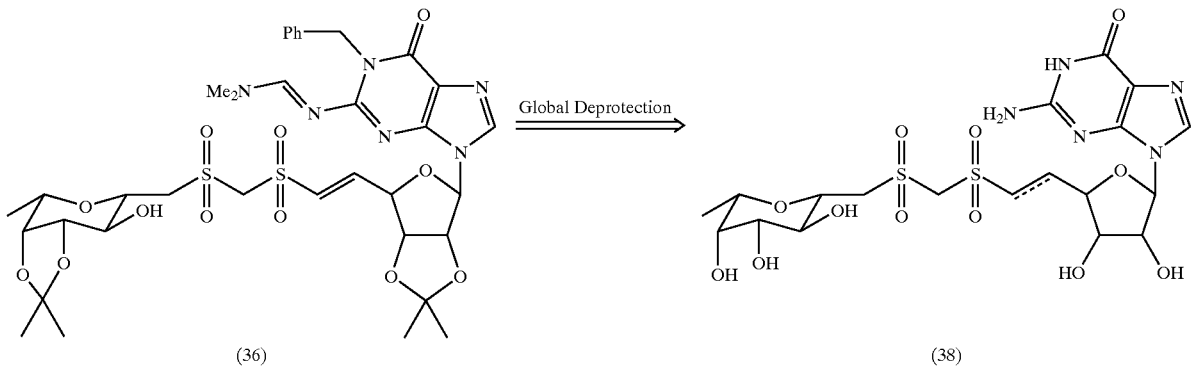

(36)                                                      (38)

a protected form of guanosine, the 5'-furanosyl aldehyde sugar that serves as the activating nucleoside for GDP-Fucose, has been prepared by reacting 32 with N,N-dimethylformamide dibenzyl acetal in DMF for 3 h at 80° C. Dess-Martin oxidation affords 33, which then can be condensed with a suitable fucosyl-C-glycoside bis-sulfone phosphonate 30 yielding 36. Global deprotection of 36 gives the targeted enzyme substrate analog 38 both with and without a double bond, depending on the deprotection strategy. Various deprotection strategies can be used but, in general, such strategies should proceed in a manner such as shown in Reaction Equation G above.

As seen in Reaction Equation H below, an alternative strategy for selective condensation involves stepwise addition employing reagent 42, which can be prepared by the reaction of 40 with potassium permanganate. Deprotonation of 42 with LiBr/DBU can give a single anion that can be condensed with a suitably protected fucose derivative 26. Subsequent oxidation of intermediate 44 then can give the bis-sulfone 46, which then can be reacted with 34 to yield 36.

Sulfonimide analogs, represented by Compound 10, where n preferably is 0, $R_1$ preferably is a nitrogen atom, and preferably $R_3$ is $R_2$, also have been synthesized as fucosyl transferase inhibitors. These compounds preferably are prepared by reacting an amine with methane sulfonyl chloride to give 48, as illustrated by the following Reaction Equation I:

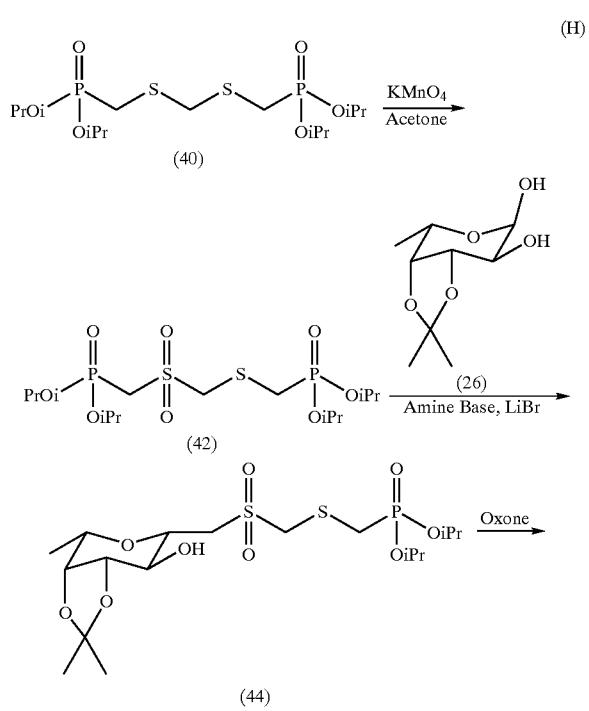

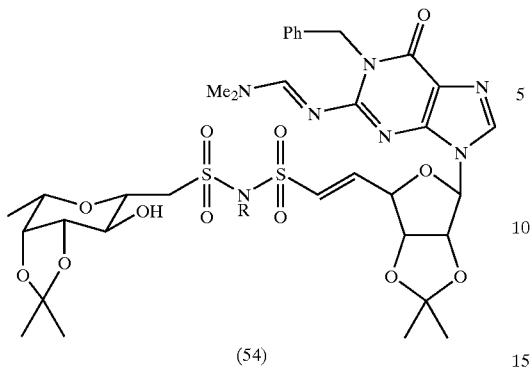

(54)

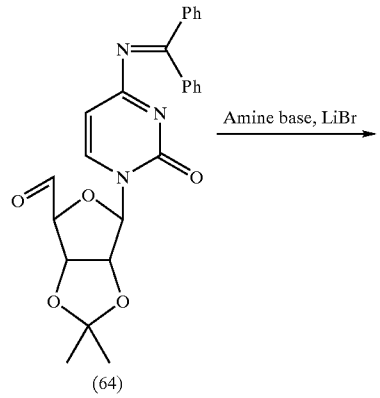

(64)

Reactant 48 can be treated with three equivalents of base and reacted with diethyl chlorophosphate to generate 50, a derivative of Compound 10. Compound 50 behaves similarly to other derivatives of Compound 10 and can undergo condensation with fucose to give 52, which then can be reacted with 34 to afford 54.

In accordance with still other aspects of these embodiments of the present invention, monosulfones which exhibit inhibitory properties can be synthesized. For example, the synthesis of the C-glycoside monosulfone of N-acetyl neuraminic acid (NeuAc) is suitably illustrated by the following Reaction Equation J:

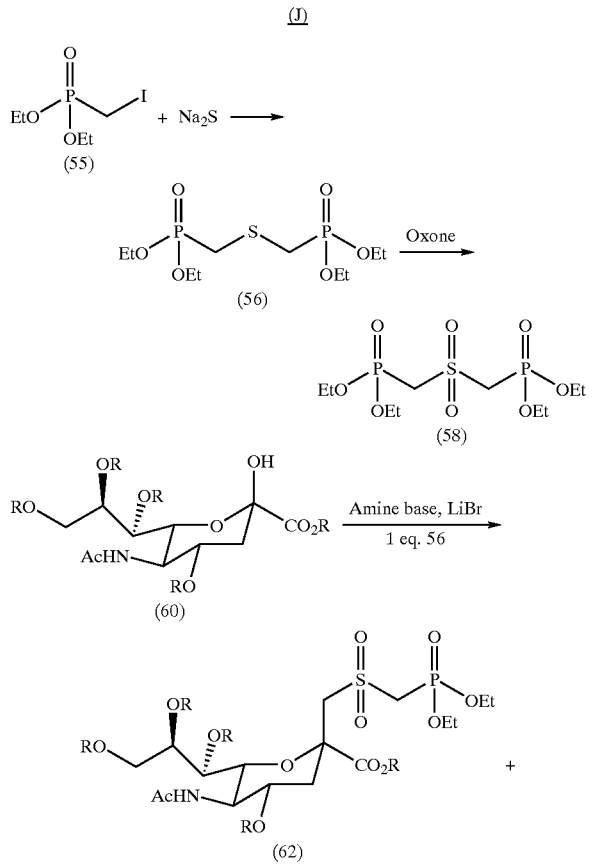

As shown above, the bis-phosphonate sulfide reagent 56 preferably is prepared by the reaction of commercially available diethyl iodomethylphosphonate 55 with disodium sulfide. Subsequent oxidation with OXONE (namely, a compound whose active ingredient is potassium peroxymonosulfate, available from DuPont under the OXONE trademark) can provide the sulfone 58. Selective reaction of a suitably protected NeuAc derivative 60 with 58 yields 62. Condensation of 62 with the aldehyde 64 forms 66, which upon deprotection can provide the target molecule 68. Suitable selectivity can be achieved by using two equivalents of base, one equivalent of NeuAc 60, and one equivalent of 58. As illustrated by Reaction Equation K below, the phosphonate anion 58 attacks the ketone of NeuAc 60 and, in the presence of an α,β unsaturated sulfone capable of undergoing Michael addition, undergoes elimination of diethyl phosphate, thereby yielding the desired product. While bis-addition is possible, single addition can be achieved by limiting the ratios of reagent to carbonyl compound to about 1:1. The intermediate Michael acceptor can undergo either a 6-exo-trig 62 or a 7-endo-trig 70 cyclization and both are favored according to Baldwin's rules. However, six-membered ring-formation may be kinetically favored. If the axial sulfone phosphonate does not form preferentially, then modification of the NeuAc ester R group may be one means for gaining stereochemical control of the anomeric center.

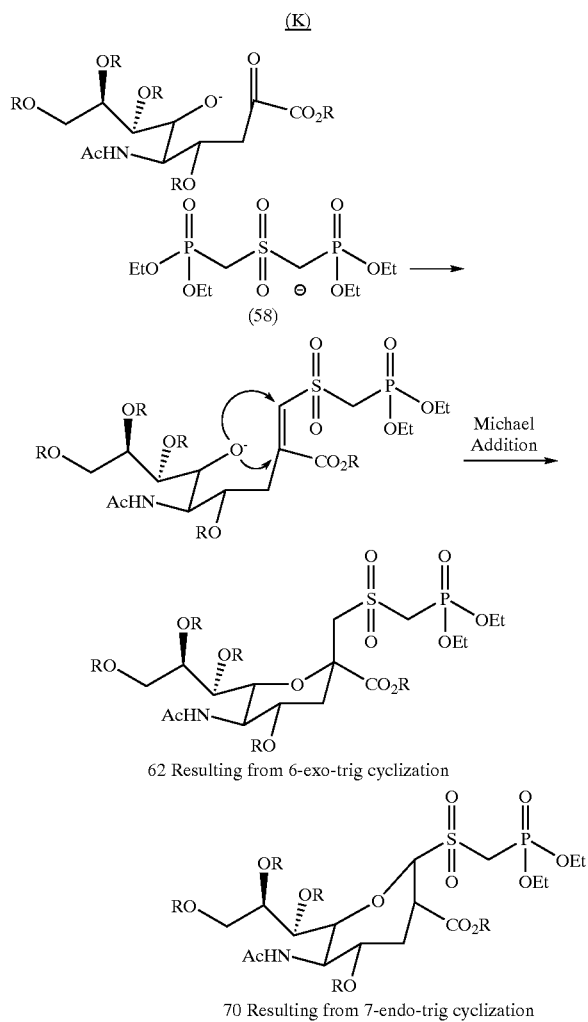

It should be appreciated that while the foregoing examples are illustrative of various mechanisms and reactions by which suitable C-glycoside sulfone isosteres of GDP-fucose and CMP-NeuAc can be prepared, these are merely exemplary embodiments of the present invention. The novel reagents of various aspects of the present invention may be utilized in a variety of ways, and the subject sulfone isosteres and analogs prepared in other manners, as may be now known or hereafter devised by those skilled in the art.

Synthesis of Disulfone-Linked Catechol-Based Enzyme Inhibitors

In addition to providing an efficient means for synthesizing C-glycosidic substrate analogs targeting enzymes involved in tumor metastasis, the novel disulfone reagents of the instant invention also provide a rapid synthetic sequence into diverse classes of compounds that target inhibition of various other enzymes, such as enzymes used by the human imnmunodeficiency virus (HIV), by acting as analogs of the natural enzyme substrates. These classes of compounds include, but are not limited to, the following: (1) symmetrical and/or unsymmetrical disulfones based on the known catechol inhibitors of certain enzymes, such as HIV integrase (HIV-IN); and (2) non-nucleoside inhibitors of other enzymes, as shown in Table 3 below.

TABLE 3

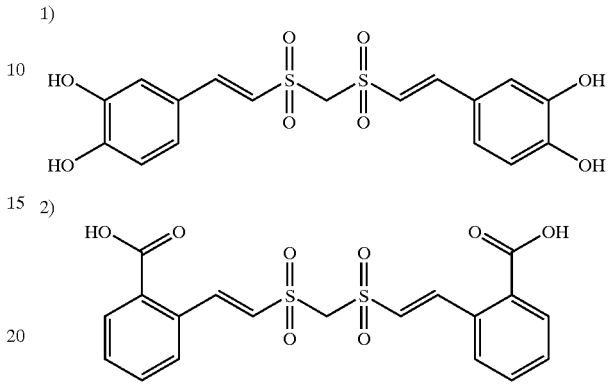

In the case of synthesizing disulfone-linked catechol-based inhibitors of particular enzymes, such as HIV-1 integrase for example, a novel disulfone reagent and a suitably selected and, in most cases, suitably protected benzaldehyde are caused to undergo condensation, preferably under mildly basic conditions, and preferably followed by deprotection, if applicable, to yield the target catechol-based enzyme inhibitor, such as an inhibitor of HIV integrase. Any suitable protection and deprotection strategies may be employed to render particular functional groups present on the selected benzaldehyde unreactive during the condensation reaction. Preferably, protection of the benzaldehyde is accomplished through acetylation or methylation, and deprotection is consequently achieved through deacetylation or demethylation. As described above, the preferred mildly basic reaction conditions can be created by any means known and practiced by those skilled in the art; however, in accordance with various aspects of the present invention, such conditions are preferably created by utilizing a source of lithium cations, such as lithium chloride or lithium bromide for example, and a suitable amine base, such as diisopropylethyl amine (DIEA), or 1,8-diazabicyclo[5.4.0]undec-7-ene (DBU). Alternatively, any suitable base having a pKa of about 15 or higher can be used.

Synthesis of disulfone-linked catechol-based enzyme inhibitors, such as inhibitors of HIV integrase for example, can be accomplished in a one step (symmetrical) or two step (unsymmetrical) synthesis followed by deprotection, if applicable, as illustrated by Equation L below. In accordance with various aspects of the present invention, an HEW condensation reaction of a novel disulfone reagent with an excess amount of a suitably selected aldehyde and a suitable base can produce symmetrical catechol-base inhibitors of such enzymes as HIV-IN. An HEW reaction of an aldehyde with an excess amount of a novel disulfone reagent and a suitable base can produce mono-substituted analogs which, when reacted with another suitably selected aldehyde, can produce unsymmetrical catechol-based inhibitors of enzymes such as HIV-IN.

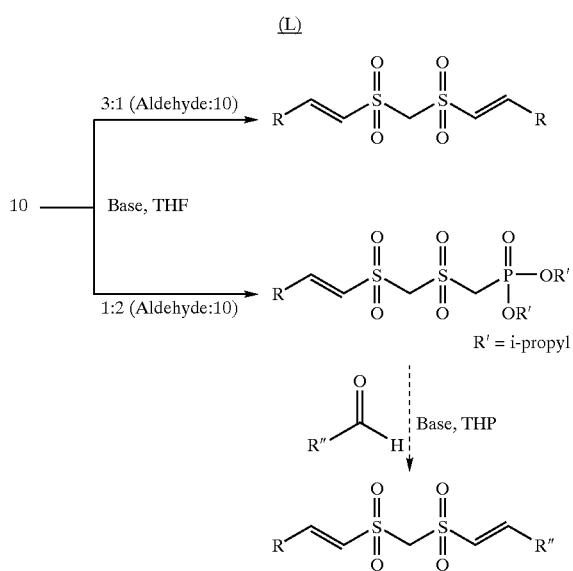

In accordance with various aspects of this embodiment of the present invention, a novel disulfone reagent can be used to synthesize disulfone-linked catechol-based inhibitors of certain enzymes, such as HIV integrase for example, as illustrated by the following Reaction Equation M:

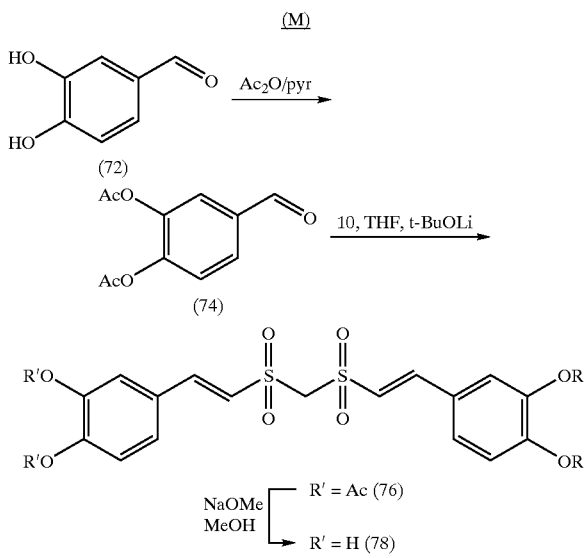

Preferably, the synthesis of catechol-based inhibitors of enzymes such as HIV-IN begins by selecting a suitable benzaldehyde, such as the commercially available 3,4-dihydroxy benzaldehyde 72 for example, and implementing a suitable protection strategy, such as acetylation of the hydroxyl groups on 3,4-dihydroxy benzaldehyde 72 with acetic anhydride in pyridine to form 74. Preferably, a Horner-Emmons-Wittig olefination reaction is carried out, which is then preferably followed by a suitable deprotection strategy, such as deacetylation, if applicable, to generate the target disulfone-linked catechol derivative, such as 76 and/or 78.

The following working example is illustrative of a method for preparing exemplary embodiments 76 and 78, shown generally in Reaction Equation M above, of a catechol-based enzyme inhibitor, such as an inhibitor of HIV-IN, using a novel disulfone reagent in accordance with the various aspects of the present invention;

Example 1

Step 1

Monosubstitution (2-Napthaldehyde): 220 mg of Compound 10 (0.44 mmol), 182 mg LiBr (2.09 mmol), and 230 mL DIEA (1.32 mmol) is dissolved in THF (5 mL), then 32 mg (0.21 mmol) of 2-naphthaldehyde is added, and the solution is left to sit for 20 hours. Addition of approximately 0.5 mL of acetic acid is followed by removal of the solvent and column chromatography (2:1 hexanes: ethyl acetate), which gives 42 mg (42%) of the monosubstituted product.

Step 2

Bis-substitution (Benzaldehyde): 10.55 mg (0.44 mmol) of NaH is added to 6 mL of isopropanol and stirred for 5 min., then 100 mg (0.2 mmol) of Compound 10 is added, and the reaction is stirred for an additional 15 min. 61 μL (0.6 mmol) of benzaldehyde is then added, and the reaction is stirred for 21 hours. After evaporation of the solvent, the crude product is subjected to column chromatography to yield 50.9 mg (73%) of the bis substituted compound.

Step 3

Reaction of Methyl 5-aldehydo-2,3-O-isopropylideneribofuranose: 83 mg (0.198 mmol) of Compound 10 is dissolved in 2 μL of THF followed by addition of 330 μL (0.330 mmol) of a 1M solution of lithium t-butoxide in THF. 40 mg (0.165 mmol) of Methyl 5-aldehydo-2,3-O-isopropylideneribofuranose is then added, and the solution is stirred for 2 hours. After the addition of 200 mL of acetic acid and evaporation of the solvent, the residual solid is subjected to column chromatography (6:1 up to 3:1 hexanes: ethyl acetate) to give 52.8 mg of a 1.81: 1 mixture of bis:mono substitution.

Step 4

3,4-diacetoxybenzyaldehyde: To a solution of 3,4-dihydroxybenzaldehyde in 20 mL of pyridine 2.0 g (14.4 mmol) is added 5.30 mL (57.9 mmol) acetic anhydride, which is then stirred for 1.5 h. Removal of solvent in vacuo, followed by extraction from water/ethyl acetate gives an oil that is subjected to column chromatography (1:1 hexanes: ethyl acetate) to yield approximately 1.5 g of the target catechol derivative compound as a clear oil.

Step 5

Compound 76: To a solution of 98 mg (0.196 mmol) of disulfone Compound 10 in 3 mL THF is added 588 mL of a 1M solution of lithium t-butoxide in THF. The solution is left to sit for 10 min., then 165 mg (0.743 mmol) of 3,4-diacetoxybenzaldehyde in 1 mL THF is added, and the reaction is left to sit for 30 minutes. Approximately 100 μL of acetic acid is then added, and the solvents removed in vacuo to yield a crude oil which is subjected to column chromatography to yield 83.1 mg of a 4.2:1 mixture of disubstituted 60% (Compound 76): 14% 14% monosubstituted product.

Step 6

Compound 78: To a solution of Compound 76 in 3 mL of methanol is added a catalytic amount of sodium methoxide, and the solution is stirred for 20 minutes. Dowex 50WX8-100 strongly acidic resin is then added, and the solution is stirred for 5 minutes. The solution is then filtered and the solvent removed in vacuo to give a quantitative yield (NMR analysis) of the target disulfone-linked catechol derivative compound having a bis-hydroxylation pattern on each of the catechol rings.

In general, suitable substituted benzaldehyde derivatives which can be used in accordance with the various aspects of the present invention to prepare suitable catechol-based enzyme inhibitors can include, but are not limited to, those represented by the following Formula:

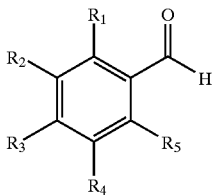

In this Formula, $R_1$, $R_2$, $R_3$, $R_4$, and $R_5$ can be the same or different and preferably represent any chemical element or chemical group such as hydrogen, methoxy (i.e., $OCH_3$), acetyl (i.e., $OCCH_3$), bromine, iodine, nitro (i.e., $NO_2$), COOH, $SO_3H$, $OSO_3H$, $P(O)(OH)_2$, or $OP(O)(OH)_2$. In addition, $R_1$, $R_2$, $R_3$, $R_4$, and $R_5$ preferably also may represent suitable salts and esters, such as suitable salts and esters of COOH, $SO_3H$, $OSO_3H$, $P(O)(OH)_2$, or $OP(O)(OH)_2$ for example. Exemplary substituted benzaldehyde derivatives that can be used in synthesizing disulfone-linked catechol-based enzyme inhibitors, such as inhibitors of HIV-IN, include, but are not limited to, the following:

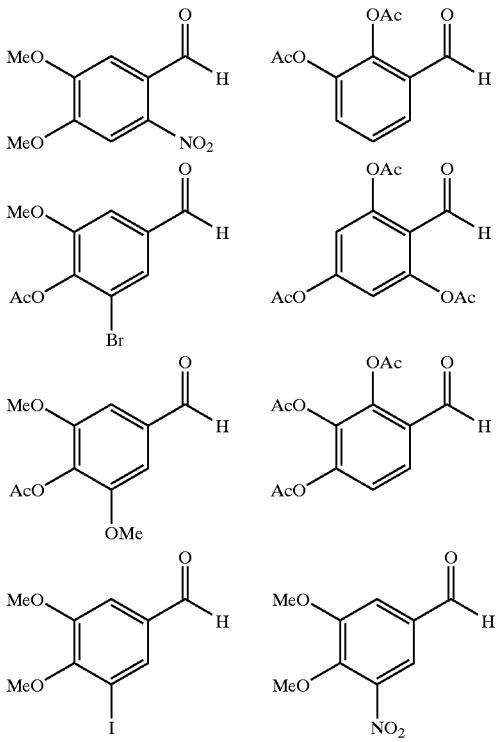

All of the above benzaldehydes are commercially available. Those available as the phenol preferably are suitably protected, such as by acetylation and/or methylation for example, prior to coupling with a novel disulfone reagent in accordance with the various aspects of the several embodiments of the present invention. Preferably, deprotection, such as by deacetylation and/or demethylation for example, then can provide the desired target compound.

Disulfone-Linked Catechol-Based HIV-1 Integrase Inhibitors

In accordance with the various aspects of the several embodiments of the present invention, novel disulfone reagents can be used to synthesize a new class of potent disulfone-linked catechol-based inhibitors of HIV integrase (HIV-IN). In accordance with one aspect of this embodiment of the present invention, a disulfone-linked catechol derivative is provided which may be represented by the following Formula representing Compound 80:

(80)

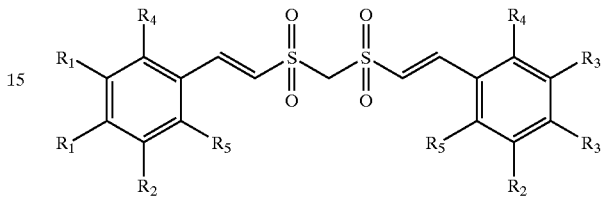

In Compound 80, $R_1$ can be the same or different and preferably represents any suitable chemical element or chemical group, such as hydrogen, hydroxyl (i.e., OH), acetyl (i.e., $OCCH_3$), methoxy (i.e., $OCH_3$), bromine, iodine, nitro (i.e., $NO_2$), COOH, $SO_3H$, $OSO_3H$, $P(O)(OH)_2$, or $OP(O)(OH)_2$. $R_2$ can be the same or different and preferably represents any suitable chemical element or chemical group, such as hydrogen, hydroxyl (i.e., OH), acetyl (i.e., $OCCH_3$,), acetyl (i.e., $OCCH_3$,), methoxy (i.e., $OCH_3$), bromine, iodine, nitro (i.e., $NO_2$), COOH, $SO_3H$, $OSO_3H$, $P(O)(OH)_2$, or $OP(O)(OH)_2$. $R_3$ can be the same or different and preferably represents any suitable chemical element or chemical group, such as hydrogen, hydroxyl (i.e., OH), acetyl (i.e., $OCCH_3$ or OAc), methoxy (i.e., $OCH_3$ or OMe), bromine, iodine, nitro (i.e., $NO_2$), COOH, $SO_3H$, $OSO_3H$, $P(O)(OH)_2$, or $OP(O)(OH)_2$, In addition, $R_1$, $R_2$, $R_3$, $R_4$, and $R_5$ preferably also may represent suitable salts and esters, such as suitable salts and esters of COOH, $SO_3H$, $OSO_3H$, $P(O)(OH)_2$, or $OP(O)(OH)_2$ for example. No particular double bond geometry (for example, cis or trans) is intended by the structure of Compound 80.

It should be understood that the disulfone-linked catechol-based compounds of the subject invention may be modified, and, as a result, a variety of derivatives are possible and also come within the scope of the present invention. For example, derivatives of the inventive disulfone-linked catechol-based Compound 80 can include both symmetrical and unsymmetrical disulfone-linked catechol-based substrate analogs for inhibiting HIV-IN. A symmetrical catechol analog may be represented by Compound 80 where $R_1=R_3$ and $R_2$ is the same, such as where $R_1$ and $R_3$ preferably are both hydroxyl and $R_2$ preferably is hydrogen for example. An unsymmetrical catechol analog may be represented by Compound 80 where $R_1$ and $R_3$ preferably are different and $R_2$ can be either the same or different, such as where $R_1$ is hydroxyl, $R_3$ is methoxy, and $R_2$ is hydrogen for example. It should be understood that these examples of symmetrical and unsymmetrical disulfone-linked catechol-based HIV-IN inhibitor compounds are merely illustrative of the several derivatives of Compound 80 and are not intended as limiting. One skilled in the art will appreciate that various derivatives of Compound 80 are possible, and all will come within the scope and spirit of the present invention.

As described above, the disulfone-linked catechol-based inhibitors of HIV integrase of the present invention are synthesized by causing a novel disulfone reagent and a suitably selected and, in most cases, suitably protected benzaldehyde to undergo an HEW condensation reaction, preferably under mildly basic conditions, and preferably followed by deprotection, if applicable, to yield the target catechol-based HIV-IN inhibitor. Any suitable protection and deprotection strategies may be employed to render particular functional groups present on the selected benzaldehyde unreactive during the condensation reaction. Preferably, protection of the benzaldehyde is accomplished through acetylation or methylation, and deprotection is preferably achieved through deacetylation or demethylation. As described above, the preferred mildly basic reaction conditions can be created by any means known and practiced by those skilled in the art; however, in accordance with various aspects of the present invention, such conditions are preferably created by utilizing a source of lithium cations, such as lithium chloride or lithium bromide for example, and a suitable amine base, such as diisopropylethyl amine (DIEA), or 1,8-diazabicyclo[5.4.0]undec-7-ene (DBU). Alternatively, any suitable base having a pKa of about 15 or higher can be used.

Generally, a particular compound's HIV integrase inhibitory potency can be measured by observing the effects of that compound on the integrase enzyme's catalytic activity. HIV integrase has two catalytic functions, (1) 3'-processing, which removes a dinucleotide unit from the 3'-ends of viral DNA; and (2) DNA strand transfer, which translocates the 3'-processed viral DNA strands from the cytoplasm to the nucleus, where they are integrated into the host's DNA. These two catalytic steps can be measured in an in vitro assay which employs a purified recombinant integrase and a 21-mer duplex oligonucleotide substrate corresponding to the U5 region of the HIV long terminal repeat (LTR) sequence. This assay permits simultaneous measurement of inhibition constants for both 3'-processing and DNA strand transfer. Inhibitory concentrations (i.e., $IC_{50}$ values) are determined based on an observed 50% reduction in enzymatic activity in cell-free assays. (See e.g, Zhao H., Neamati N., Mazumder A., Sunder S., Pommier Y., ad Burke T. "Arylamide Inhibitors of HIV-1 Integrase" *J. Med. Chem.* 1997, 40, 1186–1194), Compound 76 (an acetylated derivative of Compound 80), Compound 78 (a symmetrical, hydroxylated derivative of Compound 80), and Compound 82 (an acetylated and methylated derivative of Compound 80) have been prepared in accordance with the various aspects of the present invention and have been tested in accordance with the above-described known method of testing HIV-IN inhibition. These tests show that these compounds are potent HIV-IN inhibitors, as the following $IC_{50}$ values against HIV-IN demonstrate:

Compound 76, $R_1=R_3=OAc$ and $R_2=H$, $IC_{50}=73-77$ μM.

Compound 78, where $R_1=R_3=OH$ and $R_2=H$, $IC_{50}=4-6$ μM.

Compound 82, where $R_1=R_3=OAc$ and $R_2=OMe$, $IC_{50}=4$ μM.

Thus, disulfone-linked catechol-based HIV-IN inhibitors can be prepared in accordance with the various principles of the present invention. This inhibition is believed to be the result of the disulfone-linked catechol analog's ability to bind successfully to the HIV-IN active site, such as through its ability to bind manganese and magnesium, metals present at the HIV integrase active site.

Experimental evidence of Mn binding of the subject catechol inhibitors was obtained through titration studies. In these studies, Compound 10 was dissolved in 99.9% DMSO-$d_6$ and subsequent additions of 99.99+% $MnCl_2$ in DMSO-$d_6$ were followed by $^1H$ NMR spectroscopy. The results show the integration of the various protons. Specifically, the methylene protons between the two sulfones are exchanged at a greater rate compared with the methylene between the sulfone and phosphonate and the methine of the isopropyl.

Additional studies relating to the structural and energetic differences in manganese (Mn(II)) binding to sulfone residues of the present invention also have been conducted.

Thus, the novel disulfone reagent of the present invention not only provides for the rapid synthesis of several symmetrical (as well as unsymmetrical) catechol derivatives, but also permits the use of a gem-bis-sulfone linker between the catechol derivatives to aid synergistically in the binding of metals present in the enzyme active site. Using novel disulfone reagents in accordance with the various aspects of the present invention, a rapid synthetic sequence has been developed which can be used to prepare libraries of disulfone-linked catechol compounds by simply varying the aldehyde used in the coupling of the two aryl units of the compound. The simplicity of the synthetic strategy coupled with the commercial availability of benzaldehyde derivatives uniquely permits the preparation of a large number of novel compounds that can bind an enzyme's active site and effectively inhibit its catalytic activity.

The foregoing examples demonstrate the versatility of the novel disulfone reagent of the present invention. The novel disulfone reagents can undergo reactions with any suitably protected or unprotected aldehyde selected to form a desired end product. Target compounds that may be synthesized using the disulfone reagent include, but are not limited to, enzyme substrate analogs, such as glycosyl transferase inhibitors, catechol-based enzyme inhibitors, or any other disulfone compounds now known or hereinafter devised by those skilled in the art.

While the invention has been particularly shown and described with reference to exemplary embodiments, it will be understood by those skilled in the art that various changes in form and detail may be made without departing from the spirit and the scope of the invention.

What is claimed is:

1. A compound having the formulation of:

(10)

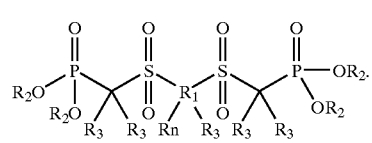

wherein n is 0, 2, or 3; wherein $R_1$ is either a carbon or a nitrogen; wherein $R_2$ is either an alkyl comprised of from about 1 to 4 carbon atoms or an arylalkyl; and wherein $R_3$ is selected from the group consisting of hydrogen, fluorine, a hydroxyl group, a double-bonded oxygen, and an epoxide group, with the proviso that n is 0 when $R_1$ is carbon and $R_3$ is a double bonded oxygen.

2. The compound of claim 1 wherein $R_2$ is selected from the group consisting of methyl ethyl, isopropyl, and tert-butyl.

3. The compound of claim 1 wherein $R_2$ is selected from the group consisting of monosubstituted arylalkyl, disubstituted arylalkyl, trisubstituted arylalkyl, tetrasubstituted arylalkyl, and pentasubstituted arylalkyl.

4. A pharmaceutically acceptable derivative of a compound according to claim 1.

* * * * *

UNITED STATES PATENT AND TRADEMARK OFFICE
CERTIFICATE OF CORRECTION

PATENT NO.    : 6,498,277 B1
DATED         : December 24, 2002
INVENTOR(S)   : Jacqueline Gervay-Hague et al.

It is certified that error appears in the above-identified patent and that said Letters Patent is hereby corrected as shown below:

<u>Column 30,</u>
Line 58, "methyl ethyl" has been replaced with -- methyl, ethyl --.

Signed and Sealed this

Thirteenth Day of May, 2003

JAMES E. ROGAN
*Director of the United States Patent and Trademark Office*